United States Patent
Auberger et al.

(10) Patent No.: US 9,022,965 B2
(45) Date of Patent: May 5, 2015

(54) KNEE ORTHOSIS, AND METHOD FOR CONTROLLING A KNEE ORTHOSIS

(75) Inventors: Roland Auberger, Wien (AT); Kelvin B. James, Edmonton, CA (US)

(73) Assignee: Otto Bock Healthcare GmbH, Duderstadt (DE)

( * ) Notice: Subject to any disclaimer, the term of this patent is extended or adjusted under 35 U.S.C. 154(b) by 90 days.

(21) Appl. No.: 12/993,798

(22) PCT Filed: May 20, 2009

(86) PCT No.: PCT/DE2009/000734
§ 371 (c)(1),
(2), (4) Date: Nov. 19, 2010

(87) PCT Pub. No.: WO2009/140956
PCT Pub. Date: Nov. 26, 2009

(65) Prior Publication Data
US 2011/0071452 A1    Mar. 24, 2011

(30) Foreign Application Priority Data
May 20, 2008 (DE) .......................... 10 2008 024 748

(51) Int. Cl.
*A61F 5/00* (2006.01)
*A61F 5/01* (2006.01)

(52) U.S. Cl.
CPC ............. *A61F 5/0125* (2013.01); *A61F 5/0111* (2013.01)

(58) Field of Classification Search
USPC .......... 602/5, 16, 20, 21, 23, 26, 27; 128/882; 601/5, 33, 34, 35
See application file for complete search history.

(56) References Cited

U.S. PATENT DOCUMENTS

| | | | | | |
|---|---|---|---|---|---|
| 3,976,057 | A | * | 8/1976 | Barclay | 601/34 |
| 4,241,730 | A | * | 12/1980 | Helfet | 602/26 |
| 4,256,097 | A | * | 3/1981 | Willis | 602/16 |
| 5,144,943 | A | * | 9/1992 | Luttrell et al. | 601/34 |
| 5,252,102 | A | * | 10/1993 | Singer et al. | 623/24 |
| 5,337,737 | A | * | 8/1994 | Rubin et al. | 601/33 |

(Continued)

FOREIGN PATENT DOCUMENTS

| | | |
|---|---|---|
| DE | 3911780 A1 | 10/1990 |
| DE | 69209476 T2 | 1/1997 |

(Continued)

OTHER PUBLICATIONS

PCT International Search Report for International Patent Application No. PCT/DE2009/000734, mailed Nov. 12, 2009.

*Primary Examiner* — Anhtuan T Nguyen
*Assistant Examiner* — Raymond E Harris
(74) *Attorney, Agent, or Firm* — Holland & Hart

(57) ABSTRACT

A knee orthosis and a method for controlling a knee orthosis including a thigh structure having a fastening structure to be fixed to a thigh, a lower leg structure which is pivotally coupled to the thigh rail using a joint mechanism and has a fastening structure to be fixed to a lower leg as well as a foot piece for supporting a foot, and an actuator device between the thigh structure and the lower leg structure. The fastening points of the actuator on the thigh structure and lower leg structure and the center of rotation of the joint mechanism form a triangle. The fastening points are arranged on the structures such that the connecting line between a fastening point and the center of rotation in an angular position of the knee in which the lower leg is bent at an angle ranging from 0° to 90° relative to the thigh.

24 Claims, 8 Drawing Sheets

(56) References Cited

U.S. PATENT DOCUMENTS

| | | | |
|---|---|---|---|
| 5,352,190 A * | 10/1994 | Fischer et al. | 602/26 |
| 5,383,939 A | 1/1995 | James | |
| 5,547,464 A | 8/1996 | Luttrell et al. | |
| 5,728,172 A * | 3/1998 | Krieger | 623/44 |
| 6,377,178 B1 | 4/2002 | DeToro et al. | |
| 6,500,138 B1 | 12/2002 | Irby et al. | |
| 6,666,837 B2 | 12/2003 | Weihermuller | |
| 6,908,488 B2 | 6/2005 | Passivaara et al. | |
| 7,578,799 B2 * | 8/2009 | Thorsteinsson et al. | 602/5 |
| 7,628,766 B1 * | 12/2009 | Kazerooni et al. | 602/16 |
| 7,947,004 B2 * | 5/2011 | Kazerooni et al. | 602/16 |
| 7,985,193 B2 * | 7/2011 | Thorsteinsson et al. | 602/16 |
| 2004/0068215 A1 * | 4/2004 | Adelson et al. | 602/26 |
| 2004/0225242 A1 | 11/2004 | Lidolt et al. | |
| 2007/0233279 A1 * | 10/2007 | Kazerooni et al. | 623/24 |
| 2008/0287850 A1 * | 11/2008 | Adarraga | 602/26 |
| 2009/0076618 A1 | 3/2009 | Auberger | |

FOREIGN PATENT DOCUMENTS

| | | |
|---|---|---|
| DE | 29914375 U1 | 12/1999 |
| DE | 19859931 A1 | 7/2000 |
| DE | 20217355 U1 | 1/2003 |
| DE | 10311189 A1 | 10/2004 |
| DE | 60015384 T2 | 10/2005 |
| DE | 102004030570 A1 | 1/2006 |
| DE | 60122483 T2 | 3/2007 |
| DE | 102006012716 B3 | 1/2008 |
| WO | 0143669 A1 | 6/2001 |
| WO | 2006037101 A2 | 4/2006 |

* cited by examiner

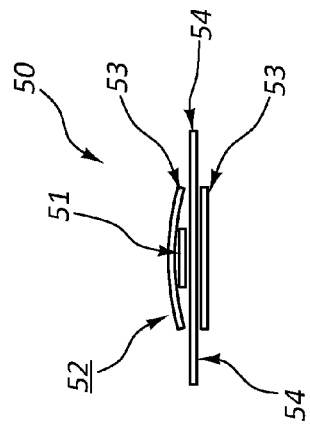
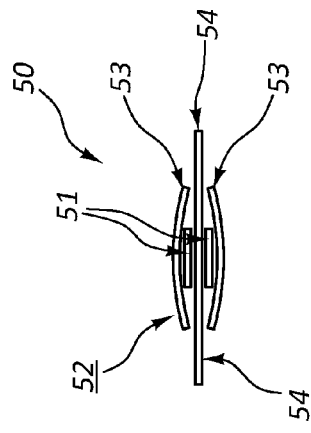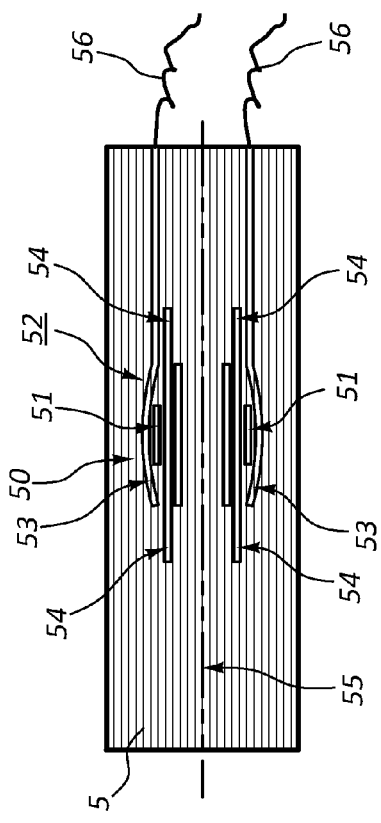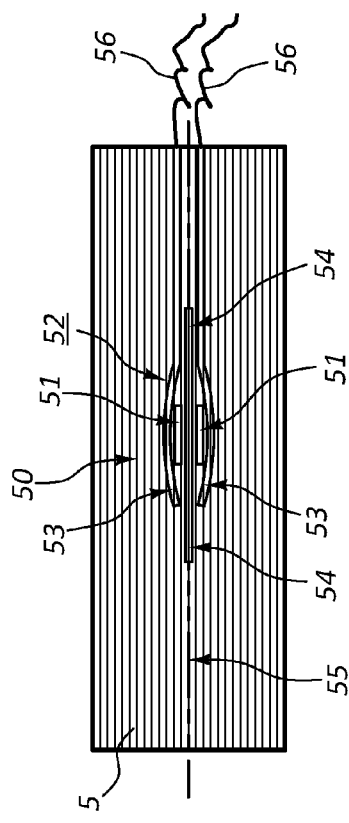

KNEE ORTHOSIS, AND METHOD FOR CONTROLLING A KNEE ORTHOSIS

The invention relates to a knee orthosis with a thigh structure, in particular a thigh rail, which has a fastening means for securing to a thigh, with a lower leg structure, in particular a lower leg rail, which is coupled pivotably to the thigh structure via a joint mechanism and has a fastening means for securing to a lower leg, and, if appropriate, a foot part for supporting a foot, and with an actuator unit between the thigh structure and the lower leg structure, and a method for controlling such a knee orthosis.

Knee orthoses are used to support or replace a function of a leg. The orthoses form an outer frame or partial frame and are applied to the leg. In cases of injuries to the ligaments or muscles, and in cases of paralysis, orthoses serve to stabilize the joint and, if appropriate, to limit the flexion angle or extension angle of the parts of the limb connected via the knee joint. Generally, the knee orthoses have a rail for the thigh and a rail for the lower leg, and they are secured to the thigh and lower leg by fastening means, such as buckles or straps.

In cases of paralysis of the leg or corresponding injuries, provision is made for the foot also to be fixed within the orthosis. For this purpose, a foot shell is provided which is secured to the lower leg structure or is formed thereon.

DE 601 22 483 T2 describes a dynamic, electromechanical orthosis device with a wrap spring clutch which, on the basis of data from sensors that are arranged in the plantar area of the foot shell, releases the joint mechanism between the thigh part and the lower leg part. A kinematic sensor is likewise provided that generates an electrical signal, which is determined on the basis of the relative position and movement of the thigh structure to the lower leg structure. This signal is used to monitor whether a wrap spring is actuated or released.

DE 10 2006 012 716 A1 describes a joint mechanism with which a movement about an axis is released or blocked. A sensor device is provided that measures forces, moments and/or angle position of the upper and lower parts to each other and is coupled to a control unit which, as a function of the measured parameters, activates an actuator and braces a spiral spring in order to block or release the joint.

DE 202 17 355 U1 describes an orthosis for external supporting and guiding of a knee joint, with a heel and foot part arranged on a lower leg structure, which is connected to a thigh structure via a joint mechanism. A locking mechanism is provided, which can be actuated by means of the force of the foot and activates the locking mechanism when the foot is set down.

DE 299 14 375 U1 describes an orthosis joint with a thigh rail and a lower leg rail which at one end engage with each other via one or more common pins or by means of teeth in the orthosis joint. End stops are present in the orthosis joint and are adjustable across an angle range. Upon flexion or extension in the orthosis joint, a constant or dynamic braking action can be performed, which takes place pneumatically, hydraulically or by means of an elastic element. The braking action is effected in particular via elastic stops.

DE 600 15 384 T2 describes a support device that replaces the existence or function of a limb and is composed of at least two parts connected to each other by an artificial joint, and a control device for the joint. A sensor is provided that detects an angle of inclination relative to a fixed line of a part connected to the joint. The sensor is coupled to the control device, which is arranged in such a way that it influences the joint on the basis of data transmitted by the sensor and relating to the angle of inclination. In addition to a prosthesis, the support device can also be designed as an orthosis.

The in some cases very complex devices take up a lot of space, particularly in the mediolateral orientation. The object of the present invention is to make available a knee orthosis which, in addition to having sufficient functionality, can also provide an improved cosmetic quality.

According to the invention, this object is achieved by a knee orthosis and by a method for controlling a knee orthosis. Advantageous embodiments and developments of the invention are described in the respective dependent claims.

The knee orthosis according to the invention with a thigh structure, which has a fastening means for securing to a thigh, with a lower leg structure, which is coupled pivotably to the thigh structure via a joint mechanism and has a fastening means for securing to a lower leg, and, if appropriate, a foot part for supporting a foot, and with an actuator unit between the thigh structure and the lower leg structure, is characterized in that the fastening points of the actuator unit, on the rails, and the center of rotation of the joint mechanism form a triangle, and the fastening points are arranged on the rails in such a way that the connecting line between the fastening points is perpendicular to a connecting line between a fastening point and the center of rotation in an angular position of the knee in which the lower leg is bent at an angle of between 0° and 90°, in particular 10° and 90°, preferably between 30° and 90°, relative to the thigh. The distances between the fastening points of the actuator unit, on the rails, and the center of rotation of the joint mechanism are fixed. However, by means of a relative movement of the fastening points to one another, on account of the pivoting of the thigh structure relative to the lower leg structure, the length of the actuator unit, for example of a hydraulic damper or of a hydraulic drive, changes. By means of a suitable arrangement of the fastening points on the rails, it is possible to provide the knee orthosis with moment characteristics dependent on the knee angle even with a constant damping of the linear actuator unit. This happens through a lever length being arranged and configured at a defined angle to the normal of the other rail, for example the lever on the lower leg structure in relation to the normal of the thigh structure which passes through the center of rotation of the joint mechanism. The corresponding angle determines how the effective lever length for the actuator or damper changes depending on the knee angle. In this way, it is possible to set the knee angle at which the obtainable resistance moment or the transmissible forces are at a maximum. This results in a suitable profile of the force or resistance moment with a non-linear relationship, such that the biomechanical lever ratios allow maximum leg support to be achieved when the leg is flexed, wherein the force applied by the actuator can be left constant. Maximum leg support thus occurs when the load on the joint mechanism or on the knee joint is very great, for example at an angle of the thigh to the lower leg of 35° to 45°. However, provision is also made for the maximum resistance moment or the maximum actuator force to be made available at a lesser or greater flexion, insofar as this is necessary or is desired by the patient. On account of the non-linear profile of the resistance moment despite a constant damping in the actuator unit, a progressive damping is obtained, particularly in the area of the stance phase flexion, and therefore a progressive stance phase damping, which can be produced without complicated control mechanisms and sensor technology if the actuator is designed as a linearly acting damper. The same applies to the design of the actuator as a drive. A progressive profile of the resistance moments in the stance phase flexion is described as comfortable by the patient, since a spontaneous buckling of the knee joint need not be feared.

In a development of the invention, the actuator is a hydraulic damper, and the valves or control means of the hydraulic damper are arranged in front of and/or behind a piston/cylinder arrangement in the direction of walking. With this arrangement of the valves and control means and also of the overflow channels, it is possible to make available a damper that has a relatively narrow shape, such that the components do not protrude much in the mediolateral orientation. This leads to increased acceptance of the orthosis, since the latter can be worn under normal clothing. The actuator unit is designed in particular as a linearly acting damper, as a result of which the entire knee orthosis can be produced more easily and more economically.

The actuator unit is preferably arranged laterally alongside the thigh or lower leg, preferably alongside the thigh, with an arrangement behind the rails of the orthosis in the direction of walking being preferred. In this way, the hydraulic mechanism can be subjected to pressure without deflection means, and the arrangement of the fastening points of the actuator on the rails permits easy adaptation to the desired moment characteristics. For example, several fastening points can be arranged on one rail, in order thereby to be able to individually adapt the moment characteristics.

In a development of the invention, the actuator unit is mounted, at least at one fastening point, via a bearing with at least two degrees of freedom. Provision is specifically made that the actuator is mounted, at least at one fastening point, via a cardan bearing with intersecting or non-intersecting axes. Because of the individual configuration of the respective orthosis, which has to be adapted to the patient, there are alignment errors in the movement axes, both in terms of the joint axis and also of the axes at the fastening points, such that the cylinder of the actuator unit moves on a cone envelope surface. Since a hydraulic damper in particular is intended only to take up axial loads, in order to ensure the stability of the actuator unit, a cardan bearing is provided at least at one fastening point, and ideally a bearing with two degrees of freedom is provided at both bearing points. Because of the high hydraulic forces that are to be transmitted, a conventional cardan bearing with intersecting axes would have to be made very solid. Because of the limited installation space, however, provision is made to divide the cardan bearing and to have the axes not intersect. This affords advantages for the design of the joint, since collisions between the hydraulics and a bearing block can be more easily avoided.

It is also possible, at the connection point between the axes, to measure the hydraulic force dependent on the knee moment, and this measured variable can be used, for example, to control the actuator. With such a joint bearing, it is possible to take up the very high hydraulic forces that occur and at the same time to keep the sizes to a minimum. Alternatively, provision is made for at least one of the bearings to be designed as a ball-joint bearing, in order to obtain, on the one hand, a low overall height and, on the other hand, a purely punctiform introduction of axial force into the actuator unit. It is thus possible to eliminate or reduce interfering bending moments, in particular moments interfering with piston/cylinder hydraulics.

An improved adaptation to the anatomical circumstances is achieved if the actuator unit is arranged, in the lateral plane, tilted about a defined angle. In this way, the actuator or hydraulic damper can be mounted lying tightly on the thigh.

In addition to this, or also separately, the foot part can have a dorsal spring, on which or in which at least one sensor is arranged for detecting the acting forces, for example the bending load, and thus for detecting the ankle moment. These sensor data can be used to change the action of the damper unit via an actuator and to change the damping in addition to the constructive damping characteristics. In the design of the actuator unit as a drive or a combination of drive and damper, the data are used to change the behavior of the actuator unit. Likewise, a knee angle sensor, knee moment sensor and an absolute angle sensor can be mounted on the orthosis for determining the spatial orientation of at least of one of the rails. The data from the sensors can be used together or separately for controlling the actuator unit. Such an arrangement of sensors for controlling the resistance moment profiles or the behavior of the actuator unit can also be used independently of the above-described geometric arrangement of the actuator unit.

The control means for changing the behavior of the actuator unit is coupled to the sensors and is used, for example, to change the damping resistance or the applied force in the actuator unit.

Joint kinematics can be provided via which the actuator unit is articulated on the thigh and/or lower leg structure. The actuator unit can also be articulated directly on the thigh and/or lower leg structure, and in both cases provision is made for a pivotability and/or displaceability of the joint kinematics or of the actuator unit. The pivotability or displaceability is in the lateral plane, and the fastening points of the actuator unit, on the thigh and lower leg structure, and the center of rotation of the joint mechanism also form a triangle.

The movement axis of the orthosis between the thigh and lower leg structures can be fixed by the midpoints of two ball joints, if the thigh and lower leg structures are connected to each other by ball joints. Alternatively, the thigh and lower leg structures can also be connected to each other by a cardan joint.

The pivot angle of the joint mechanism in the lateral plane can be fixed by a medial support joint, which can be a hinge joint, cardan joint or ball joint.

The lever between the rotation axis of the joint mechanism and the adjacent fastening point of the actuator unit can be formed by two ball joints coupled via at least one connecting rod.

The method for controlling a knee orthosis with a thigh structure, a joint mechanism and a lower leg structure, which has a foot part, is characterized in that an active moment, in particular ankle moment, within the orthosis is determined, and the resistance of the actuator unit is changed as a function of the moment, in particular ankle moment. In addition or as an alternative, the actuator unit can be changed as a function of a measured or calculated knee moment, the knee angle, that is to say the position of thigh structure and lower leg structure to each other, or of the spatial orientation at least of a thigh or lower leg structure. It is possible in this way to control the stance and swing phases in patients with paralysis, in whom the leg is no longer controllable at will. By means of the modifiable resistance moment, for example via a hydraulic actuator, every desired knee moment can be generated, thereby permitting stance phase flexion and alternating descent of inclines or stairs. In active actuator units, the movement can be correspondingly supported in a targeted and efficient manner.

In a development of the invention, the sensor signals generated within the orthosis are additionally used to generate impulses for functional electrostimulation of the remaining muscles. In this case, the measured values determined by the orthosis are used to establish the strength and/or timing of the stimulation impulses from a unit connected to the control device and permitting functional electrostimulation. In this way, the remaining muscles can be activated in a targeted manner in order to improve the movement profile and to support or replace the actuator device.

An illustrative embodiment of the invention is explained in more detail below with reference to the attached figures, in which:

FIG. 9 shows a sensor on a substrate plate;

FIG. 10 shows an example of the arrangement of sensors according to FIG. 9 in a connection element;

FIG. 11 shows a variant of the sensor according to FIG. 9; and

FIG. 12 shows an example of the arrangement of the sensor according to FIG. 11.

Figure 1:
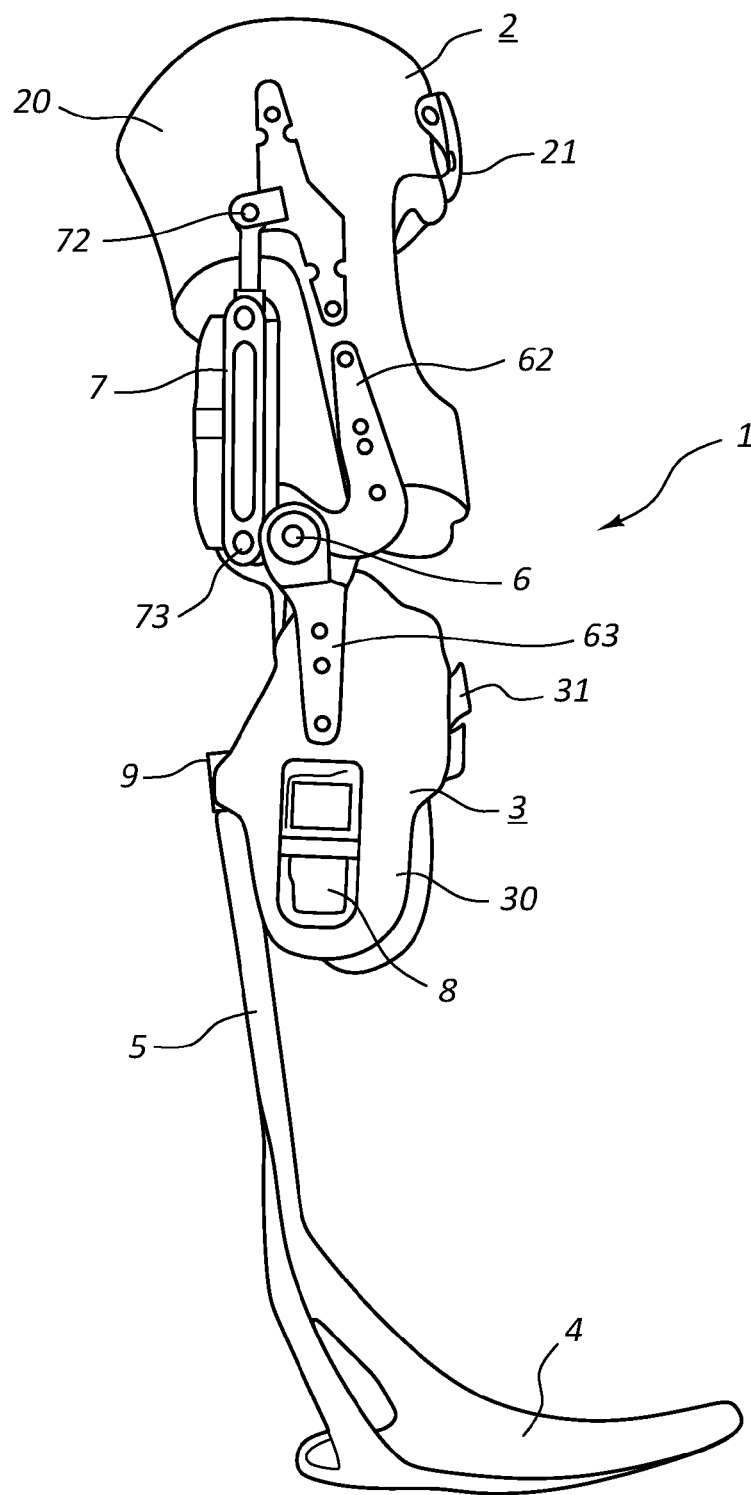
FIG. 1 shows a schematic side view of a knee-ankle-foot orthosis in side view.

In FIG. 1, an orthosis device 1 in the form of a knee-ankle-foot orthosis is shown in a schematic representation. The orthosis device 1 has an upper part 2 in the form of a thigh structure, and a lower part 3 in the form of a lower leg structure. The thigh structure 2 and the lower leg structure 3 are connected to each other via a joint mechanism 6 so as to be able to pivot about a joint axis. A foot part 4 is secured to the lower leg structure 3 via a connection element 5. The connection element 5 is arranged in a receiving means 9 located on the dorsal face of the lower leg structure 3.

The thigh structure 2 is composed of a main body in the form of a receiving shell, which can be secured to a thigh by fastening means 21. The fastening means are, for example, buckles, clasps or hook-and-loop fasteners, which can be placed across an opening within the thigh structure 2 and thus close the thigh structure 2. The opening can be frontal or dorsal. Fastening means 31 are likewise arranged on the lower leg structure and can be closed frontally below the knee joint around the lower leg.

The joint mechanisms 6 can be arranged both medially and laterally on the orthosis device 1, and the thigh structure 2 and the lower leg structure 3 are secured to the joint mechanism 6 by joint structure elements 62, 63. A control device 8 for controlling an actuator unit 7 is arranged on the lower leg structure 3 and, on the basis of a program and various sensor data, changes parameters within the actuator unit, in order thereby to increase or decrease the damping or to adjust the applied force. As an alternative to arranging the control unit 8 on the lower leg structure 3, it can also be arranged on the thigh structure 2. The actuator unit 7 is designed as a hydraulic or pneumatic actuator unit with a piston and a cylinder. In the illustrative embodiment shown, the proximal end of a piston rod is arranged at an upper attachment point 72 on the thigh structure 2, and a lower attachment point 73 of an actuator housing is arranged as the distal bearing point of the actuator unit 7 on a proximal end of the lower leg structure 3, in the area of the lower joint structure elements 63. The foot part 4 can be designed in one piece with the connection element 5 and can be secured replaceably in a receiving means 9 on the lower part 3, or the connection element 5 can also be secured to a separately formed foot part 4. The connection element 5 can also be formed in one piece with the lower leg structure 3.

In the illustrative embodiment shown, the actuator unit 7 is arranged only on the lateral side of the orthosis device 1, as an alternative to a lateral and medial arrangement of two joint mechanisms 6, if appropriate with two actuator units 7.

Figure 2:
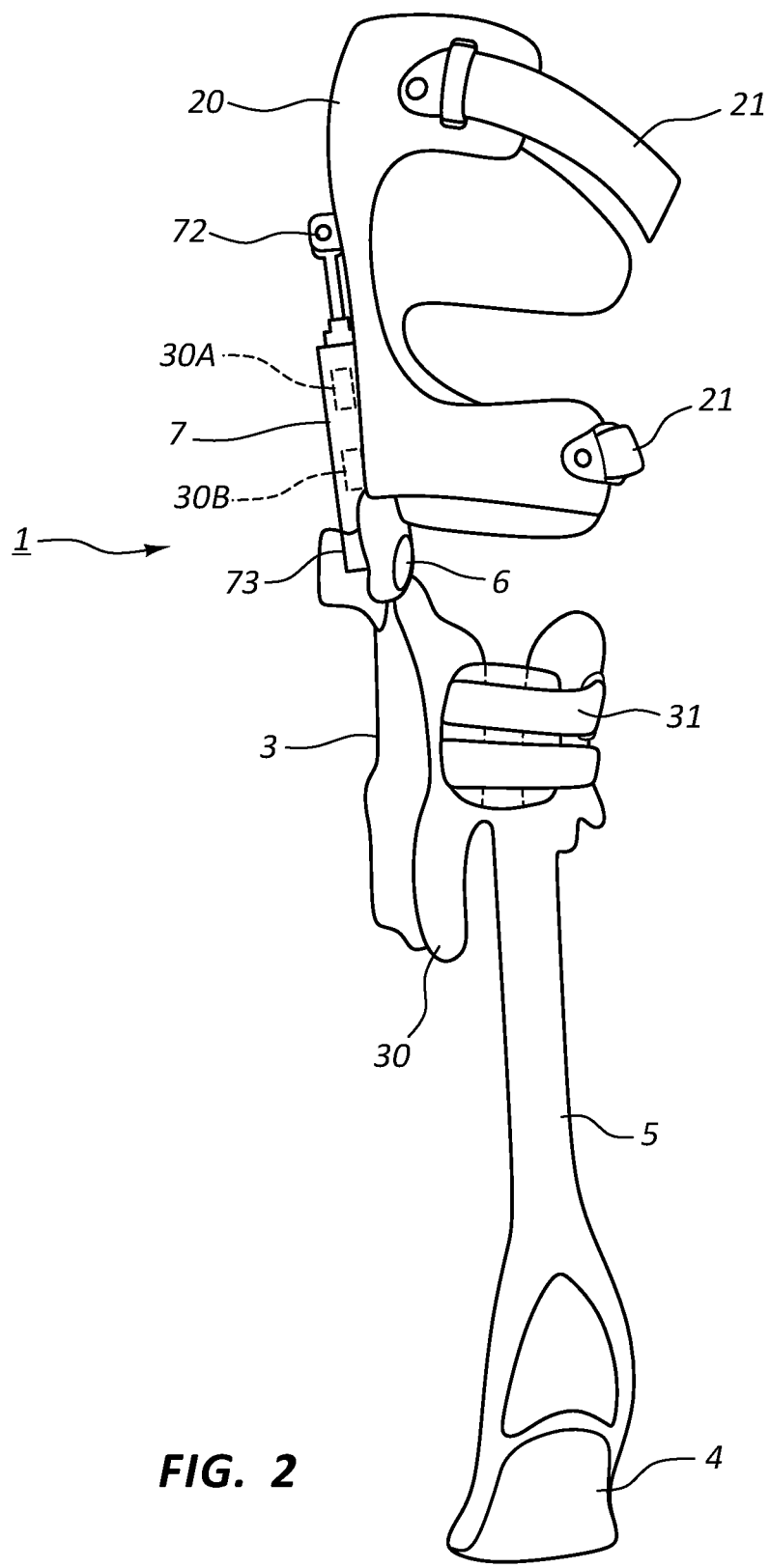
FIG. 2 shows a schematic representation of the orthosis in a front view.

In FIG. 2, the orthosis device 1 according to FIG. 1 is shown in a front view. It will be seen here that the thigh structure 2 is composed of a shell-shaped main body 20, on which fastening means 21 in the form of straps are arranged. The lower leg structure 3 is correspondingly provided with a main body 30, which can be secured by the fastening means 31 to the lower leg (not shown) of a person wearing the orthosis. An orthosis device 1 for a right leg is shown in FIG. 2, and the joint mechanism 6 is arranged laterally on one side of the orthosis device 1. It can also be seen from FIG. 2 that the main bodies 20, 30 of the thigh structure 2 and lower leg structure 3, respectively, are closed dorsally.

Figure 3:
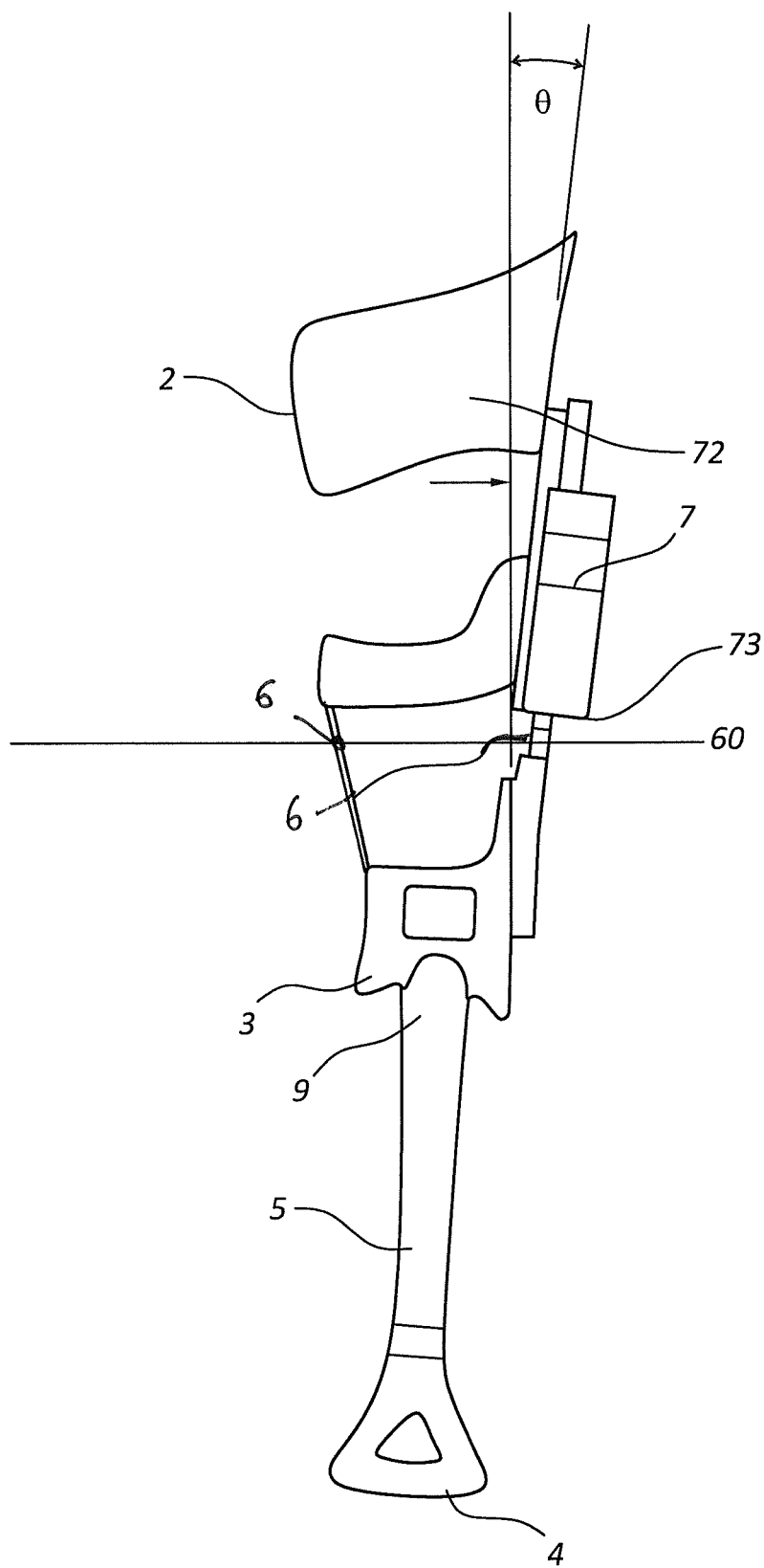
FIG. 3 shows an orthosis device in a view from the dorsal direction.

In FIG. 3, the orthosis device 1 is shown in a rear view. Extending through the joint mechanism 6 is a joint axis 60, which is flush with an anatomical rotation axis of compromise and about which the upper part 2 and the lower part 3 are mounted so as to pivot relative to each other. The joint axis 60 is shown horizontally in FIG. 3, which in reality would only exceptionally be the case. The actuator unit 7 is arranged directly on the thigh structure 2. It will be seen from FIG. 3 that the longitudinal course of the actuator unit 7 is at an angle θ to the vertical, such that the axes of the proximal and distal attachment points 72, 73 of the actuator do not run parallel to the knee axis. This angle θ corresponds to the ilio-tibial angle about which the actuator unit 7 has to be pivoted out of the sagittal plane. The pivot axis runs in the anterior-posterior direction. The ilio-tibial angle θ can be up to 30°, depending on the manner of securing and on the anatomy of the orthosis wearer.

Figure 4A:
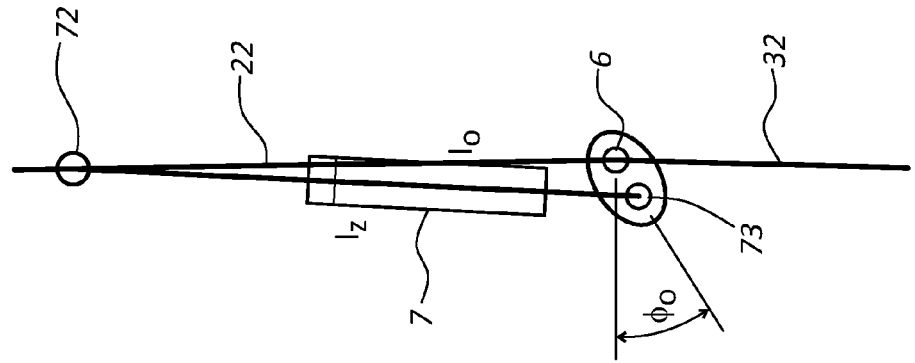
FIGS. 4a and 4b show schematic representations of the orthosis when standing and sitting.
Figure 4B:
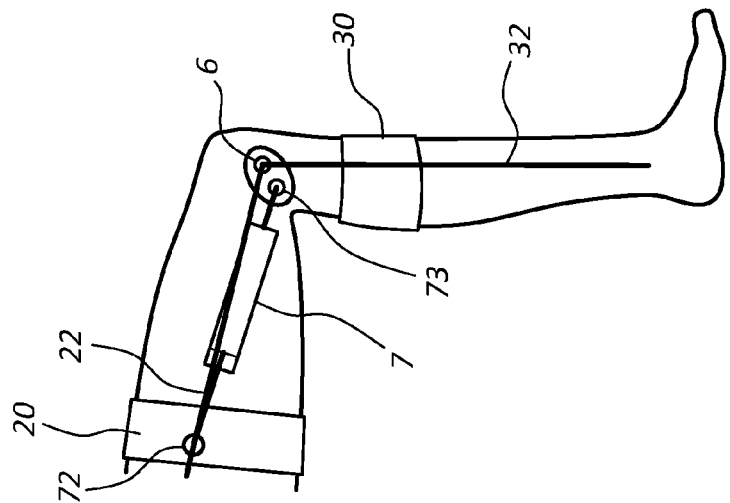

FIGS. 4a and 4b show a schematic representation of an applied orthosis device 1, in a standing position in FIG. 4a, and in a seated position in FIG. 4b. The orthosis device 1 is shown in a simplified manner with a thigh rail 22 and a lower leg rail 32, which are mounted so as to be pivotable relative to each other about the joint mechanism 6. The thigh rail 22 is secured to the thigh by a corresponding fastening means 20, while the lower leg rail 32 is secured to the lower leg by the corresponding fastening means 30. The thigh rail corresponds to the thigh structure, while the lower leg rail corresponds to the lower leg structure. The actuator unit 7 is arranged laterally and dorsally with respect to the rails 22, 32, the upper fastening point 72 of the actuator unit 7 being arranged on the thigh rail 22, and the lower fastening point 73 of the actuator unit 7 being arranged on the lower leg rail 32. The joint mechanism 6 at the same time forms the center of rotation of the two rails 22, 32 with respect to each other. The lower fastening point 73, which forms the distal bearing of the actuator unit 7, is at a distance in the dorsal direction from the center of rotation of the joint mechanism 6, this distance being embodied via an obliquely downwardly directed lever. In the embodiment shown, the fastening point 73 of the actuator unit 7 lies below the center of rotation of the joint mechanism 6 when the lower leg rail 32 is perpendicular.

FIG. 4b is a schematic representation of the state when an orthosis wearer is seated with the orthosis fitted. The angle between the thigh rail 22 and the lower leg rail 32 is greater than 90°. It will be seen from FIG. 4b that the actuator unit 7 is arranged laterally alongside the thigh of the orthosis wearer. It is thus possible for the leg to be completely flexed without the actuator unit 7 getting in the way. Likewise, with such an arrangement of the actuator unit 7, the orthosis is not bulky, which means that the orthosis can be worn inconspicuously. In FIGS. 4a and 4b, the foot part for supporting the foot is not shown. It is also possible, in principle, for the orthosis 1 to be provided without a foot part.

Figure 5:
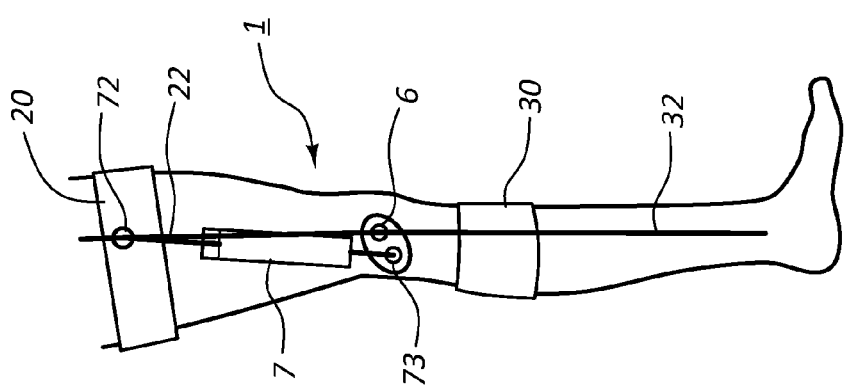
FIG. 5 shows a diagram of the arrangement of the actuator unit.
Figure 6:
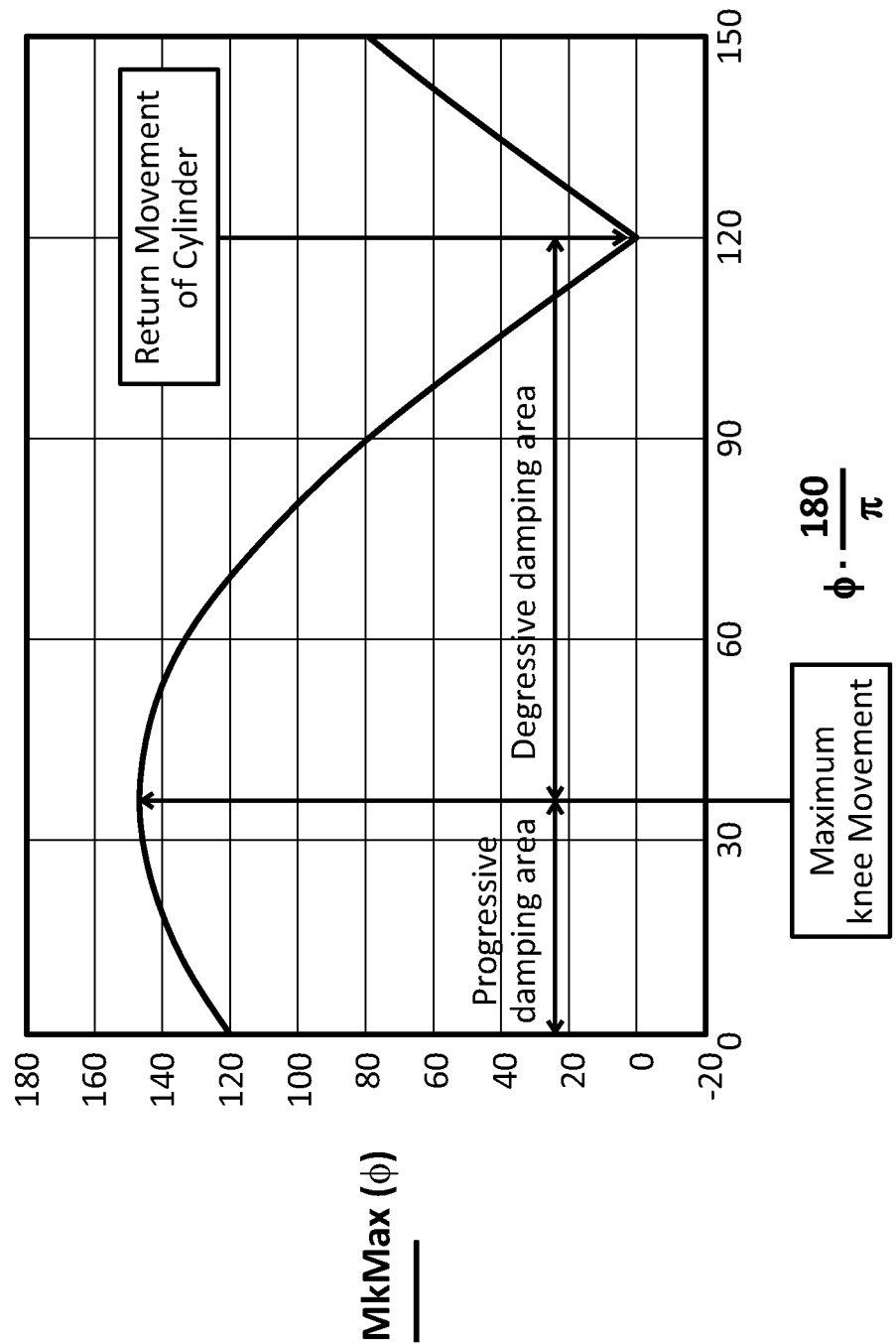
FIG. 6 shows a profile of the moment over the knee flexion.

FIG. 5 shows the basic geometric arrangement of the actuator unit 7 on the rails 22, 32. The hydraulic piston is mounted at its upper end on the upper bearing point 72, for example in a ball-and-socket bearing. At the lower end of the actuator unit 7, it is supported at the lower bearing point 73, which is coupled to the lower leg rail 32. The thigh rail 22 and the lower leg rail 32, or the upper part and the lower part of the orthosis device, are coupled to each other in the joint mechanism 6 so as to be able to pivot about a joint axis. The fastening point 73 of the lower bearing is offset dorsally by the distance $l_H$ in relation to the center of rotation or axis of rotation of the joint mechanism 6, such that the two fastening points 72, 73 and the center of rotation of the joint mechanism 6 form a triangle. The side between the lower fastening point 73 and the center of rotation 6 is at an angle $\Phi_0$ of ca. 30° with respect to the side formed between the upper fastening point 72 and the center of rotation 6, when the orthosis device 1 is extended. It is only after the thigh structure 2 or the thigh rail 22 has pivoted about an angle corresponding approximately to $\Phi_0$ in the direction of flexion that the actuator unit 7, or the side between the upper fastening point 72 and the lower fastening point 73, is perpendicular to the connecting line $l_H$ between the lower fastening point 73 and the center of rotation of the joint mechanism 6. The lever $l_H$ between the rotation axis of the joint mechanism 6 and the adjacent fastening point 73 of the actuator unit 7 can be embodied by two ball joints coupled via at least one connecting rod. This angle $\Phi_0$ lies between 0° and 90°, in particular between 10° and 90°, and preferably between 30° and 90°, and is chosen such that it corresponds to the angle at which the maximum knee moment between the thigh and the lower leg of the orthosis wearer is reached or is intended to be reached. A schematic profile of the knee moment over the flexion angle is illustrated in FIG. 6. An angle of 30° is assumed as the angle $\Phi_0$. It will be seen from FIG. 6 that a progressive damping area is present from the extended position at 0° up to a flexion angle of 35°, such that, even with a linear configuration of the actuator unit 7, a progressive damping is achieved on account of the changing geometry. The deviation of the end angle of the progressive damping area from $\Phi_0$ results from the change in the lengths of the actuator unit during flexion.

At the start of the flexion, that is to say across the first 35° of flexion, the knee moment increases as far as an angle $\Phi_0$, which arises from the trigonometric relationships and corresponds approximately to $\Phi_0$, until the connecting line between the upper articulation point 72 and the lower articulation point 73 is perpendicular to the connecting line between the lower articulation point 73 and the center of rotation of the joint mechanism. On account of the purely axial force that the actuator unit 7 can provide counter to a flexion of the knee, a maximum knee moment is reached when the working axis of the actuator unit 7 is perpendicular to the connecting line between the center of rotation of the joint mechanism 6 and the lower bearing point 73. Upon a further flexion of the knee, the knee moment decreases about the sine of the further pivoting, until there is a return movement of the actuator unit, that is to say when the flexion is greater than 90° plus $\Phi_0$. The knee moment then increases with the cosine if the action of the cylinder of the actuator unit or of the damper has been switched from press to pull.

Figure 7:
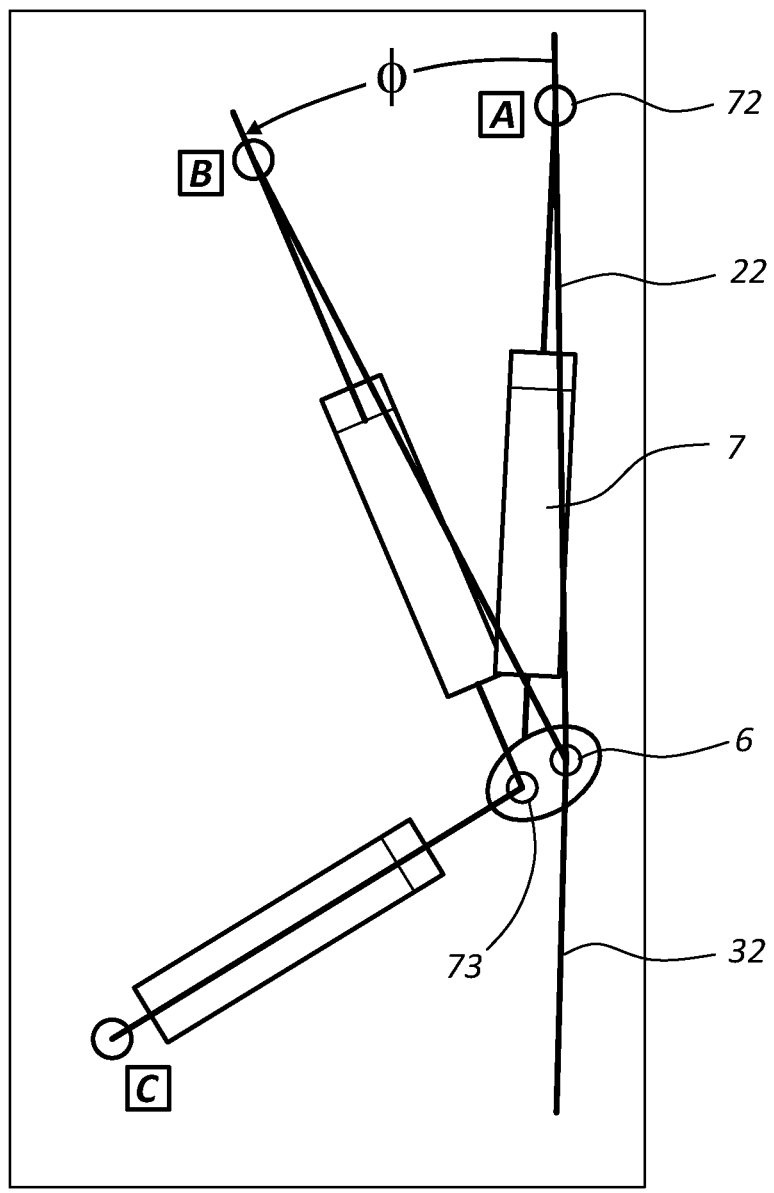
FIG. 7 shows positions of the actuator unit at different flexion angles.

Three extreme states are shown in FIG. 7. State A exists in an extended position of the leg. In position B, pivoting has taken place about the angle $\Phi$, such that the maximum knee moment is reached. In position C, the working axis of the actuator unit 7 lies on the connecting line between the lower bearing point 7 and the center of rotation of the joint mechanism 6, such that a pivoting angle of 90° plus $\Phi$ is reached. In this position, the active knee moment is equal to 0, since no lever is present, and the actuator force extends perpendicularly through the center of rotation of the joint mechanism 6.

Figure 8:
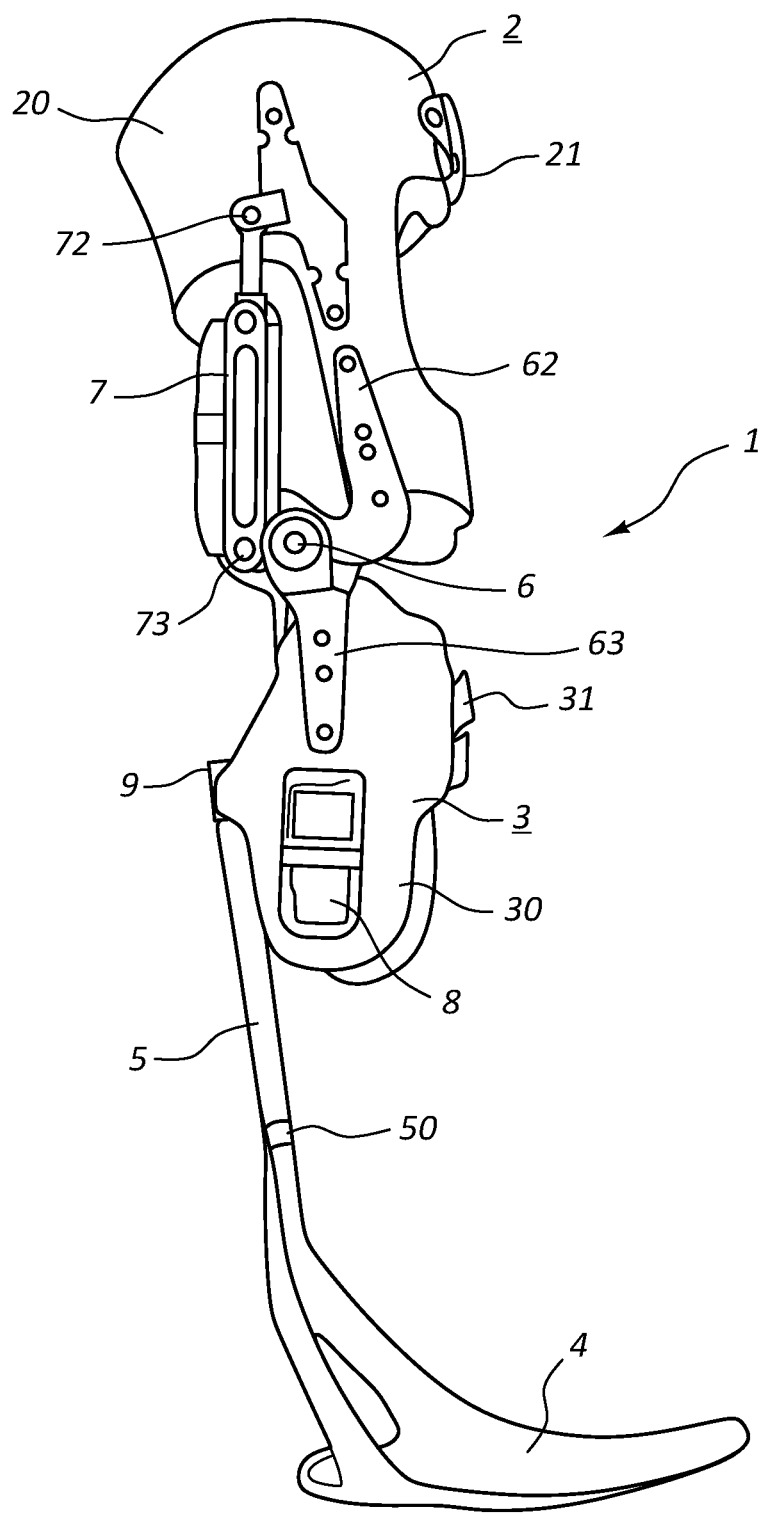
FIG. 8 shows a variant of FIG. 1.

In addition to the moment profile being influenced on the basis of the construction and arrangement of the actuator unit 7 within the joint orthosis 1 and of the special arrangement of the bearing points 72, 73 relative to the center of rotation of the joint mechanism 6 or to the joint axis 60, the damping within the joint orthosis can be controlled on the basis of sensor data. The sensor is preferably arranged in the connection element 5, which is designed as a dorsal spring, and determines the active ankle moment during standing or walking. The arrangement of the sensor 50 is shown in FIG. 8, which corresponds substantially to FIG. 1, with the difference that the sensor 50 is arranged on or in the connection element 5, which is designed as connection element between the foot part 4 and the lower leg structure 3. The sensor 50 transmits the data to the control unit 8 via which valves 30A, 30B within the actuator unit 7 as shown in FIG. 2, are then actuated. Throttle points can likewise be made larger or smaller, such that it is possible to achieve different flows of fluid and therefore degrees of damping or forces during the movement. Damping can also be achieved using electro-rheological or magneto-rheological fluids and by a corresponding change in the viscosity of these fluids.

Such control of the orthosis device 1 makes it possible, particularly in patients with paralyses, in whom the leg is present but can no longer be controlled at will, that the stance phase and swing phase can be controlled while walking. By virtue of the hydraulic actuator principle in particular, it is possible to generate any desired knee damping or flexion moment, thus permitting a stance phase flexion and alternating descent of inclines or stairs and active support of the movement. For the acceptance of such an orthosis device, it is important, in addition to functionality, that its design makes it as inconspicuous as possible, and, in particular, the extent of the orthosis device 1 in the mediolateral direction must be minimized as much as possible.

The sensor 50 for determining the active forces in the connection element 5, particularly for determining the ankle moment, can be integrated in the connection element 5. FIG. 9 is a schematic cross-sectional view showing the design of a sensor 50 with a strain gauge 51, which is secured on a substrate, in particular a metal substrate 52. The strain gauge 51 is secured in a conventional manner on the substrate 52, for example adhesively bonded, and is screened off from the environment by separating layers 53. The separating layers 53 are fixed on the substrate 52 and can be composed, for example, of a separating film or a silicone encapsulation or coating. These separating layers 53, which are arranged on the top and also on the underside of the substrate 52, avoid shearing forces being transmitted to the substrate 52 and to the strain gauge 51 secured thereon. Provided laterally alongside the separating layers 53, connection areas 54 of the substrate 52 are provided at which the substrate 52 can be connected to the surrounding composite material. These connection areas 54 come into contact with the binders of the fiber composite material and thus establish a connection to the fiber materials.

FIG. 10 is a schematic side view of the connection element 5 in the form of a bar spring element, for example. A sensor 50 with a screened-off strain gauge 51 on a substrate 52 is laminated in on each side of the neutral fiber 55. Cables 56, which are connected to the strain gauge 51, lead from the connection element 5 to an evaluation unit or the control device 8. The substrate 52 is preferably thin, for example between 0.1 mm and 0.5 mm, such that the whole arrangement of the sensor 50 with the strain gauges 51 and separating layers 53 has a thickness of less than 1 mm. The sensitivity of the sensors can be adjusted by the position inside the connection element 5, the change arising from the variation in the distance from the neutral fiber 55.

FIGS. 11 and 12 show a variant of the invention in which strain gauges 51 are arranged on both sides on the substrate 52 and are surrounded by separating layers 53. Here too, connection areas 54 are provided alongside the separating layers 53 in order to be laminated into the connection element 5. FIG. 12 is a sectional view showing the arrangement of the sensor 50 according to FIG. 11 inside the connection element 5. The sensor 50 is arranged in the neutral fiber 55 of the connection element 5, and the cables 56 lead from the connection element 5. The substrate 52 bends together with the connection element 5 and generates an output signal. Because the strain gauges 51 are arranged directly adjacent to the neutral fiber 55, a high amplification factor is needed, but there is the advantage that only a single foreign body has to be arranged inside the composite material element 5. This foreign body in the form of the sensor 50 can be easily inserted and laminated in as a completely prefabricated module, which optionally contains an electronic circuit for signal amplification and signal processing.

The connection element 5 is designed as a dorsal spring in order to increase the energy efficiency for the orthosis wearer. Like the foot part 4 applied thereto or formed integrally thereon, the connection element 5 can also be composed of a fiber-reinforced, elastic structure, for example a carbon structure, which absorbs the energy of the contact at heel strike and, upon initiation of the swing phase, releases the absorbed energy, as a result of which the initiation of the swing phase is made easier. By measurement of the deformations within the connection element 5 by the integrated sensor 50 or by several integrated sensors, which can also be integrated in the foot part 4 analogously to the integration within the connection element 5, it is possible, from the direct measurement of the deformations within the structures, to draw conclusions regarding the position of the body and the intended movement of the patient. On the basis of the determined sensor data, for example of the ankle moment or of the loads and load directions acting inside the respective structure, it is possible to make various adjustments in the actuator unit 7. Various states of the damping or of the drive are switched, wherein the state transitions are carried out as a function of the sensor signals within the connection element 5 and, if necessary, of a knee angle sensor. The knee angle, that is to say the flexion angle between the thigh structure 2 and the lower leg structure 3, can be determined either by an angle-measuring device, arranged directly on the joint mechanism 6, or with the aid of sensors which measure the position of the respective components relative to a directional component independent of the orthosis, for example relative to the force of gravity component or to the horizontal. Likewise, sensors can be provided for measuring knee moments or axial force loads, in order to further improve the control possibilities of the actuator unit.

During the rollover movement of the foot when walking, the ankle moment runs through a typical time profile during the stance phase. In the course of the rollover movement, the connection element 5 is initially deformed, i.e. "charged" with energy, after which the connection element 5 relaxes again, i.e. energy is output. Analogously to this, there is a typical profile for the knee angle and for the knee moment, and this profile can be influenced via the actuator unit 7, in particular via the actuator hydraulics, as a result of which the time profile of the energy stored in the connection element 5 can also be influenced within certain limits.

The actuator unit 7 is preferably equipped as a linear hydraulic damper unit. The damping can be adjusted via two valves separately for extension and flexion, the valves being adjusted via servo motors and an optionally interconnected gear. The receiving shells 20, 30 of the thigh structure and lower leg structure 2, 3, respectively, are likewise preferably made of a carbon fiber material, so as to be able to take up high forces without requiring a large format and without making the orthosis device 1 too heavy. The actuator unit 7 generates braking moments, with kinetic energy being converted into heat. With the orthosis device 1, it is possible to walk on the level at different speeds, to climb inclines or stairs with different gradients and to adopt different seated positions. Different operating modes can be set via corresponding operating elements on the orthosis device 1, for example by remote control or a PC interface, which can be used to call up different programs stored in the control unit 8. In a similar way, necessary software can also be loaded onto the control unit 8 or modified by an orthopedic technician.

The invention claimed is:

1. A knee orthosis, comprising:
   a thigh structure, which has a first fastening member for securing to a thigh;
   a lower leg structure, which is coupled pivotably to the thigh structure via a joint mechanism and has a second fastening member for securing to a lower leg;
   a hydraulic actuator unit between the thigh structure and the lower leg structure, the hydraulic actuator unit including fastening points, on the thigh structure and on the lower leg structure, and the center of rotation of the joint mechanism form a triangle, and the fastening points are arranged on the thigh and lower leg structures in such a way that the connecting line between the fastening points is perpendicular to a connecting line between one of the fastening points and the center of rotation in an angular position of the knee in which the lower leg is bent at an angle of between 0° and 90° relative to the thigh;
   wherein the hydraulic actuator unit and the fastening points of the hydraulic actuator unit are mounted so as to be movable or pivotable in a lateral plane, which extends laterally from a medial side to a lateral side of the knee orthosis, wherein the hydraulic actuator unit is arranged in the lateral plane, tilted about an angle θ relative to a longitudinal axis of the thigh structure when the thigh structure and the lower leg structure are aligned.

2. The knee orthosis as claimed in claim 1, wherein the hydraulic actuator unit is mounted, at least at one fastening point, via a bearing with at least two degrees of freedom.

3. The knee orthosis as claimed in claim 2, wherein the hydraulic actuator unit is mounted, at least at one fastening point, via a cardan bearing with intersecting axes or non-intersecting axes.

4. The knee orthosis as claimed in claim 1, further comprising a foot part having a dorsal spring, on which or in which at least one sensor is arranged for detecting the moment forces acting in the dorsal spring.

5. The knee orthosis as claimed in claim 4, wherein the at least one sensor is arranged for detecting the ankle moment acting in the dorsal spring.

6. The knee orthosis as claimed in claim 1, wherein valves or control members of the hydraulic actuator unit are arranged in front of and/or behind a piston/cylinder arrangement in the direction of walking.

7. The knee orthosis as claimed in claim 1, wherein a knee moment sensor and/or a knee angle sensor are arranged on the orthosis.

8. The knee orthosis as claimed in claim 1, wherein an absolute angle sensor for detecting the spatial orientation of at least one of the structures is mounted on the orthosis.

9. The knee orthosis as claimed in claim 1, wherein the thigh structure and the lower leg structure are connected to each other via a cardan joint.

10. The knee orthosis as claimed in claim 1, wherein the behavior of the hydraulic actuator unit includes a damping resistance.

11. A knee orthosis, comprising:
a thigh structure having a first fastening member configured for mounting to a thigh;
a joint mechanism having a center of rotation;
a lower leg structure pivotably coupled to the thigh structure with the joint mechanism and having a second fastening member configured for mounting to a lower leg;
an hydraulic actuator unit coupled between the thigh structure and the lower leg structure, the hydraulic actuator unit including first and second fastening points arranged at opposing first and second ends of the hydraulic actuator unit that are connected to the thigh and lower leg structures, respectively, wherein a connecting line extending between the fastening points is arranged perpendicular to a connecting line between one of the first and second fastening points and the center of rotation when the lower leg is bent at an angle of between 0° and 90° relative to the thigh;
wherein the center of rotation of the joint mechanism and the fastening points form a triangle, and either one of the first and second fastening points or the entire hydraulic actuator unit is movable or pivotable in a lateral plane, which extends laterally from a medial side to a lateral side of the knee orthosis;
wherein the hydraulic actuator unit is arranged to be articulated relative to a longitudinal axis of the thigh structure at an angle θ between 0° to 30° within the lateral plane when the thigh structure and the lower leg structure are aligned.

12. The knee orthosis as claimed in claim 11, wherein the hydraulic actuator unit includes a plurality of valves or control members to dampen motion of the hydraulic actuator unit.

13. The knee orthosis as claimed in claim 11, wherein the hydraulic actuator unit is arranged laterally alongside the thigh or lower leg in a direction of walking.

14. The knee orthosis as claimed in claim 11, wherein at least at one of the first and second fastening points are mounted via a bearing with at least two degrees of freedom.

15. The knee orthosis as claimed in claim 11, wherein at least at one of the first and second fastening points are mounted via a cardan bearing with intersecting axes, non-intersecting axes, or a ball-joint bearing.

16. The knee orthosis as claimed in claim 11, further comprising a foot part having a dorsal spring and at least one sensor arranged for detecting forces acting in the dorsal spring.

17. The knee orthosis as claimed in claim 11, further comprising at least one of a knee moment sensor and a knee angle sensor positioned on the knee orthosis.

18. The knee orthosis as claimed in claim 11, further comprising an absolute angle sensor for detecting the spatial orientation of at least one of the thigh and lower leg structures.

19. The knee orthosis as claimed in claim 11, further comprising a control member configured to adjust a damping resistance of the hydraulic actuator unit as a function of sensor signals obtained by at least one sensor.

20. The knee orthosis as claimed in claim 11, wherein the joint mechanism comprises a cardan joint or a ball joint.

21. A method for controlling a knee orthosis as claimed in claim 1, wherein an active ankle moment within the knee orthosis is determined with an ankle moment sensor which is connected to the lower leg structure, and the behavior of the hydraulic actuator unit is changed as a function of at least the ankle moment.

22. The method as claimed in claim 21, wherein the behavior of the hydraulic actuator unit is changed as a function of a measured or calculated knee moment.

23. The method as claimed in claim 21, wherein the resistance of the hydraulic actuator unit is changed as a function of the spatial orientation of at least one structure.

24. A knee orthosis, comprising:
a thigh structure, which has a first fastening member for securing to a thigh;
a lower leg structure, which is coupled pivotably to the thigh structure via a joint mechanism and has a second fastening member for securing to a lower leg;
a hydraulic actuator unit between the thigh structure and the lower leg structure, the hydraulic actuator unit including fastening points, on the thigh structure and on the lower leg structure, and the center of rotation of the joint mechanism form a triangle, and the fastening points are arranged on the thigh and lower leg structures in such a way that the connecting line between the fastening points is perpendicular to a connecting line between one of the fastening points and the center of rotation in an angular position of the knee in which the lower leg is bent at a pivot angle of between 0° and 90° relative to the thigh;
wherein the hydraulic actuator unit and the fastening points of the hydraulic actuator unit are mounted so as to be movable or pivotable in a lateral plane through an angle θ relative to a longitudinal axis of the thigh structure when the thigh structure and the lower leg structure are aligned, which extends laterally from a medial side to a lateral side of the knee orthosis, wherein the pivot angle of the joint mechanism in the lateral plane is fixed by a medial support joint, which includes one of a hinge joint, a cardan joint, and a ball joint.

* * * * *